(12) United States Patent
Munk

(10) Patent No.: US 6,613,019 B2
(45) Date of Patent: Sep. 2, 2003

(54) LIQUID MEDICATION DELIVERY DEVICE AND A METHOD OF DELIVERING AN INTENDED DOSE

(75) Inventor: Jens Aage Munk, Ølstykke (DK)

(73) Assignee: Novo Nordisk A/S, Bagsvaerd (DK)

( * ) Notice: Subject to any disclaimer, the term of this patent is extended or adjusted under 35 U.S.C. 154(b) by 19 days.

(21) Appl. No.: 09/905,147

(22) Filed: Jul. 13, 2001

(65) Prior Publication Data

US 2002/0016573 A1 Feb. 7, 2002

Related U.S. Application Data

(60) Provisional application No. 60/223,648, filed on Aug. 8, 2000.

(30) Foreign Application Priority Data

Jul. 14, 2000  (DK) .......................................... 2000 01093

(51) Int. Cl.⁷ ................................................ A61M 5/00
(52) U.S. Cl. ........................ 604/187; 604/207; 604/221; 604/246
(58) Field of Search .......................... 604/48, 500, 506, 604/93.01, 104, 118, 121, 131, 134–136, 141–144, 181, 187, 207–209, 218, 220, 221, 232, 246, 264, 272, 310–311

(56) References Cited

U.S. PATENT DOCUMENTS

| | | | | |
|---|---|---|---|---|
| 3,985,133 A | * | 10/1976 | Jenkins et al. | 128/DIG. 12 |
| 4,207,871 A | * | 6/1980 | Jenkins | 604/245 |
| 4,265,240 A | * | 5/1981 | Jenkins | 128/DIG. 12 |
| 4,335,834 A | | 6/1982 | Zepkin | |
| 4,346,606 A | * | 8/1982 | Cannon et al. | 128/DIG. 13 |
| 4,364,386 A | * | 12/1982 | Jenkins et al. | 417/63 |
| RE31,315 E | * | 7/1983 | Jenkins et al. | 417/63 |
| 4,391,599 A | * | 7/1983 | Jenkins | 604/118 |
| 4,437,859 A | * | 3/1984 | Whitehouse et al. | 604/131 |
| 4,460,079 A | * | 7/1984 | Hanks | 192/85 A |
| 4,460,353 A | * | 7/1984 | Deckert et al. | 604/31 |
| 4,529,401 A | | 7/1985 | Leslie et al. | |
| 4,617,016 A | | 10/1986 | Blomberg | |
| 4,634,431 A | | 1/1987 | Whitney et al. | |
| 4,767,399 A | * | 8/1988 | Bollish | 210/416.1 |
| 4,985,015 A | | 1/1991 | Obermann et al. | |
| 5,171,301 A | * | 12/1992 | Vanderveen | 604/141 |
| 5,423,746 A | * | 6/1995 | Burkett et al. | 128/DIG. 13 |
| 5,713,520 A | | 2/1998 | Glassey et al. | |
| 5,928,201 A | | 7/1999 | Poulsen et al. | |
| 6,050,450 A | | 4/2000 | Gardos | |

FOREIGN PATENT DOCUMENTS

| | | | | |
|---|---|---|---|---|
| DE | 1 232 655 | | 5/1968 | ............ F04B/19/00 |
| DE | 26 09 699 | | 3/1976 | ............ A61M/1/02 |
| DE | 30 26 983 A1 | * | 7/1980 | ............ A61M/5/16 |
| FR | 2 622 457 | | 11/1987 | ............ A61M/5/20 |
| GB | 2 060 131 A | * | 4/1981 | ............. F16J/9/28 |
| WO | WO 93/02720 | | 8/1992 | ............ A61M/5/00 |
| WO | WO 99/59657 | | 5/1999 | ............ A61M/5/00 |

* cited by examiner

Primary Examiner—Ira S. Lazarus
Assistant Examiner—Andrea M. Ragonese
(74) Attorney, Agent, or Firm—Marc A. Began, Esq.; Richard W. Bosk, Esq.; Reza Green, Esq.

(57) ABSTRACT

A liquid medication delivery device for, and a method of, delivering medication from a cartridge having a moveable piston at one end is disclosed. The piston has a first wall face that contacts the liquid in the cartridge and a second wall for engaging a piston rod that drives the piston. The first and second walls are moveable but the second wall tends to move more quickly then the first during administration of a dose of medication from the cartridge. To compensate for this difference in movement between the first and second wall faces, the rod first moves a distance corresponding to the amount that the first wall face must move to deliver the desired dose and then it continues to move past this position by an amount known as an overshoot distance. It is then retracted by a distance equal to the overshoot distance.

7 Claims, 1 Drawing Sheet

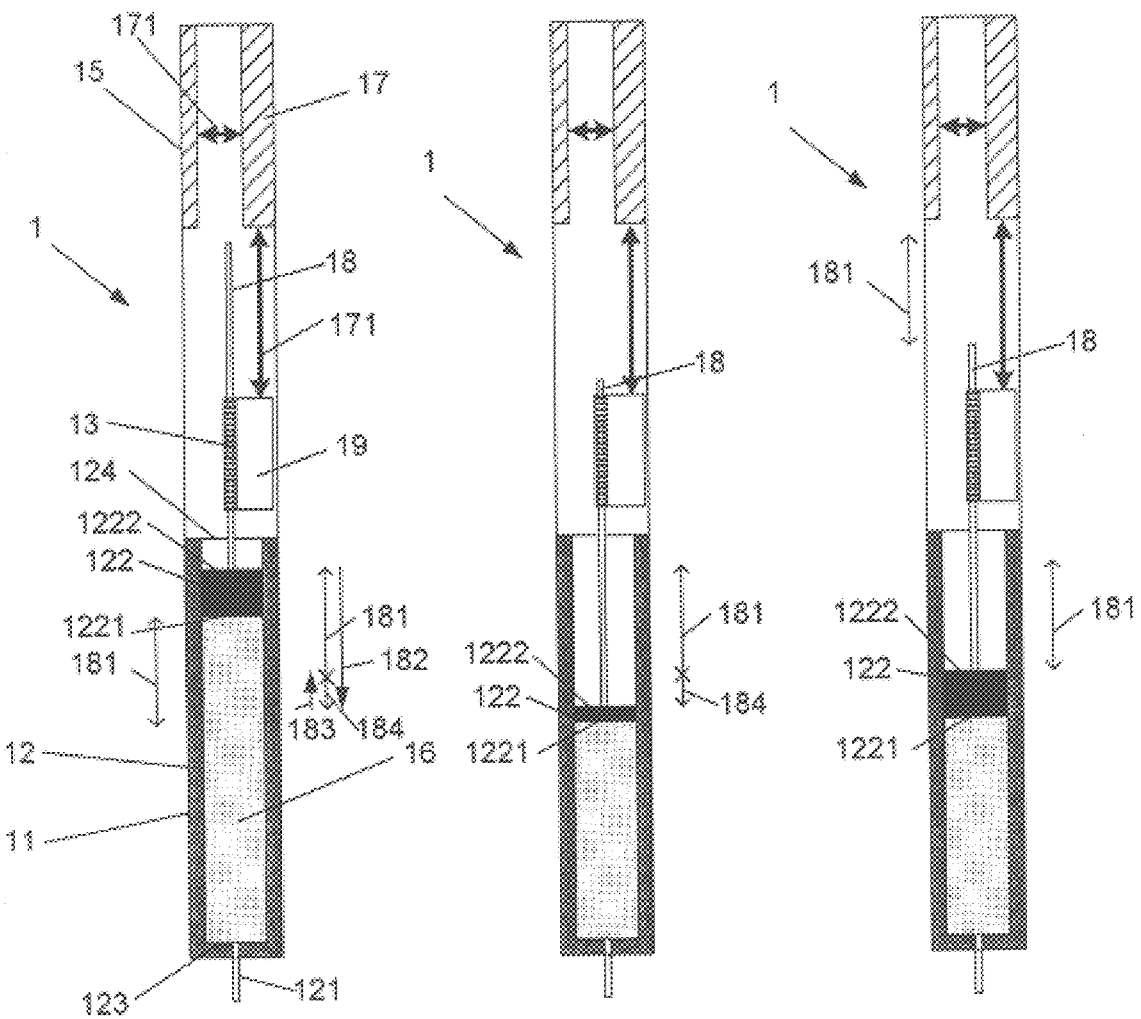
Fig. 1.a    Fig. 1.b    Fig. 1.c

LIQUID MEDICATION DELIVERY DEVICE AND A METHOD OF DELIVERING AN INTENDED DOSE

CROSS REFERENCE TO RELATED APPLICATION

This application claims the benefit of priority under 35 USC §119 of Danish Application PA 2000 01093, filed Jul. 14, 2000 and U.S. Provisional Application No. 60/223,648, filed Aug. 8, 2000; the contents of both are hereby incorporated by reference in their entirety.

BACKGROUND OF THE INVENTION

The invention relates to the delivery of a specific dose from an injection or an infusion device.

The invention relates specifically to: A liquid medication delivery device for delivering an intended dose, said delivery device including means for holding a cartridge, a cartridge for holding a liquid to be fully or partially injected into a body, said cartridge having an outlet connected to a needle at one end and a movable wall at another end, said movable wall having an inner face and an outer face, and a piston rod being operable to engage and displace said movable wall.

The invention furthermore relates to: A method of delivering an intended dose from a liquid medication delivery device, said delivery device including means for holding a cartridge, a cartridge for holding a liquid to be fully or partially injected into a body, said cartridge having an outlet connected to a needle at one end and a movable wall at another end, said movable wall having an inner face and an outer face, and a piston rod being operable to engage and displace said movable wall.

In the present context, the term 'piston rod being operable to engage and displace said movable wall' is taken to mean that the piston rod may or may not be fixed to the movable wall.

The following account of the prior art relates to one of the areas of application of the present invention, insulin dosing systems.

The use of drug administration systems for self-treatment of a disease, e.g. diabetes, is subject to many inconveniencies, such as having to meet a certain time schedule in the treatment, ensuring that the correct dose of the correct medication is delivered, etc. Of great importance to a user is the time span needed for the injection of a relevant dose, i.e. the time that the needle has to be inserted in the skin to ensure that the dose is delivered. Another very important aspect for a user is to ensure that a correct intended dose is delivered.

A well-known problem that characterizes pen and dosing systems is that usually a small drop of liquid appears at the needle tip after the needle has been removed from the skin. The size of the drop depends on many factors such as dosage speed and size, friction in the cartridge, piston condition, the time span that the needle is kept in the skin, the needle dimensions, the liquid viscosity, etc. This spill further results in a reduced dose accuracy.

Existing systems typically include a relatively inflexible medication cartridge, e.g. made of glass and a relatively flexible piston, e.g. made of rubber. During a dosing event, the piston rod (and with it the 'outer' wall of the piston, i.e. the one that engages the piston rod) will typically advance faster than the liquid medication can be delivered from the cartridge (including the outlet via a needle). This results in the piston being compressed, including the compression of possible annular sealing rings or ribs facing towards the walls of the cartridge, and including the compression of possible small elevations in the outer wall of a rubber piston (present to facilitate the separation of identical parts during production/assembly of the cartridge/delivery device). When the displacement of the piston rod is terminated, the mentioned deformations will be relaxed (i.e. the elastically deformed materials will return to their unstrained state) and, importantly, the system will continue to dose until the relaxation is completed. This represents one of the sources for observed 'afterdripping' in liquid medication delivery devices. Another source is the possible use of a soft gasket or sealing in the outlet end of the cartridge that provides the possibility of replacing the needle without introducing leaks or risk of contamination.

U.S. Pat. No. 5,713,520 discloses a hydraulically actuated fuel injector designed to provide a more abrupt ending to each injection event in order to improve performance and exhaust emission quality. The abrupt ending is achieved by allowing the residual fuel pressure to dissipate into a fuel return passage rather than dribble out of the injector nozzle.

In U.S. Pat. No. 6,050,450 a microprocessor-controlled fluid dispenser for dispensing micro size fluid droplets from a syringe in accordance with programmed shot volume increments is described. Reduced dripping from the syringe is achieved by slightly retracting the plunger to relieve pressure upon ending the compressing of the fluid by the plunger (which is a fixed extension of the piston rod and in direct contact with the liquid).

The object of the present invention is to reduce the overall injection time, while improving the dose accuracy for a liquid medication delivery system.

SUMMARY OF THE INVENTION

This is achieved according to the invention in that the piston rod is adapted to sequentially advance the outer face of said movable wall to a position corresponding to a dose that is greater than the intended one, followed by a reversal of the piston rod to allow the outer face of said movable wall to return to a position corresponding to the intended dose.

In the present context the terms 'inner' face and 'outer' face of a movable wall in a liquid medication cartridge are taken to mean the face having contact with the liquid and the opposite face (typically engaging a piston rod), respectively.

The simultaneous reduction of the overall injection time and the assurance that a correct dose is delivered reduce the inconvenience and thus contribute to the well-being of the user.

An advantage of the invention is that the amount of time the needle must be kept under the skin can be reduced and thereby the total time it takes to make the injection. A dose of say 20 IU may be injected in 1–2 seconds, but due to the drip following the injection, the needle has to stay in the skin for some time (around 6 seconds) to ensure that the drip has terminated, giving a total injection time of 7–8 seconds. The present invention may decrease the total injection time significantly (e.g. by 50–75%) contributing to the user's well-being.

The invention further reduces the drip from the needle tip of a medical injection device after the injection. This has the advantageous effect that no spill of the drug in question is disposed in the tissue or on the skin, resulting in an improved dose accuracy and a more 'clean' injection.

Further advantages of the invention are that it improves the performance of a delivery device, while allowing the use of existing (relatively low cost) components, thus increasing the quality to cost ratio.

In a preferred embodiment said delivery device comprises actuating means for generating a force or a torque, and driving means for converting said force or torque from said actuating means into a translatory movement of said piston rod.

When said actuating means comprise an electromotor, a homogeneous and stable movement of the piston rod and thus the movable wall may be achieved.

When said delivery device comprises a microcomputer at least for controlling the actuating means, it is ensured that a precise stop of the movable wall may be provided, resulting in an improved dose accuracy. The microcomputer may further be used to receive inputs from the user on intended dose or to read such data from an associated memory. A software program governing the movement of the piston may be executed by the microcomputer. Such a program may be based on empirical rules as regards the medication, the cartridge, the needle, the dose, etc., which are used in the situation in question. Several such programs, each one governing a specific combination of physical parameters, may be stored in the memory and the relevant one be executed in a given situation. Alternatively a parametrised program adapted for allowing one or more of the physical variables to be changed may be executed to control the medication delivery process. The program may alternatively be entirely founded on a theoretical basis and take into account parameters such as dosage speed and size, friction in the cartridge and needle, the viscosity of the liquid, piston characteristics, the time span that the needle is kept in the object in question, the applied pressure and the needle dimensions, etc. Alternatively the theoretical and empirical approach may be combined, e.g. by supplementing the empirical rules with theoretical ones. In a special embodiment of the invention, the medication delivery process is dynamically adapted to the present physical conditions by means of real time monitoring of decisive parameters of the process (such as piston pressure, medication temperature, etc.) fed into the program that controls the movement of the piston. In view of the differentiated compensation pattern, the microcomputer may further be used to tell the user when to remove the needle by means of an optical and/or acoustical signal.

When the cartridge is replaceable, it is ensured that the delivery device may be used in cases where the same delivery device is used repeatedly for many injections, as for example is the case in connection with a user's self-treatment of a disease such as diabetes.

In a preferred embodiment the delivery device is of a pen type.

A method of delivering an intended dose from a liquid medication delivery device, said delivery device including means for holding a cartridge, a cartridge for holding a liquid to be fully or partially injected into a body, said cartridge having an outlet connected to a needle at one end and a movable wall at another end, said movable wall having an inner face and an outer face, and a piston rod being operable to engage and displace said movable wall is furthermore provided by the present invention. When it comprises the steps of sequentially activating the piston rod to advance the outer face of said movable wall to a position corresponding to a dose that is greater than the intended one, followed by a reversal of the piston rod to allow the outer face of said movable wall to return to a position corresponding to the intended dose, it is ensured that the same advantages as outlined for the corresponding apparatus claim are provided.

When the movement of the movable wall is based on an empirical rule, it is ensured that the method may be optimized to a certain combination of physical parameters such as the medication, the cartridge, the needle, the dose, etc.

When the movement of the movable wall is determined from a model based on parameters including one or more of dosage speed and size, friction in the cartridge and needle, the viscosity of the liquid, piston characteristics, applied pressure, the time span that the needle is kept in the object in question, and the needle dimensions, it is ensured that a very flexible method that may be implemented to automatically take account of different medication, different cartridges, different needle sizes, etc. is provided.

BRIEF DESCRIPTION OF THE DRAWINGS

FIG. 1a shows a liquid medication device according to the present invention

FIG. 1b shows the device of FIG. 1a after the piston has moved a distance greater than is necessary to expel a desired dose from the device.

FIG. 1c shows the device after the piston has been retracted partially after the movement shown in FIG. 1b.

DETAILED DESCRIPTION OF THE INVENTION

The invention will be explained more fully below in connection with a preferred embodiment and with reference to the drawings in which:

FIGS. 1a–1c show a liquid medication injection device according to the invention.

The figures are schematic and simplified for clarity, and just show details which are essential to the understanding of the invention, while other details are left out.

FIGS. 1a–1c schematically show a liquid medication injection device according to the invention. FIGS. 1a, 1b, 1c illustrate the steps of an injection according to the invention exemplified by a pen type injection device (1) for delivering a controlled dose to a user.

FIG. 1a schematically shows a preferred embodiment of the invention in the form of a pen type injection device 1 having means 11 for holding a replaceable cartridge 12 containing a liquid medication 16 for injection into a user's body.

The cartridge has an outlet 121 with a needle at one end 123 and a moveable wall in the form of a piston 122 at its opposite end 124.

The piston 122 has an inner face 1221 towards the liquid and an outer face 1222 for engaging a piston rod 18 that may be linearly moved by an electromotor 19 via driving means 13. Special care is taken to avoid the use of resilient materials in the coupling volume between the piston rod and the piston. This is important to avoid further elastic after-effects that are difficult to control.

The piston rod 18 is mainly cylindrical, axially stiff, and provided with threads (not shown) that, together with a corresponding driving nut provided with a gear wheel (not shown) on its outer periphery and a corresponding cooperating gear wheel (not shown) on the motor, constitute the driving means 13 for converting movement from the motor 19 to the piston rod 18.

A microcomputer 17 (including memory and I/O interfaces) has electrical connections 171 to the electromotor 19 and the Input/Output (I/O) devices (keyboard and display) for communicating with the user. The microcomputer 17 controls the medication delivery process.

The medication delivery process comprises the step of displacing the piston 122 in the direction of the outlet 121 of the cartridge 12 to a position where the inner face 1221 of the piston corresponds to the intended one 181, whereas the outer face 1222 of the piston corresponds to a dose 184, that is greater than the intended one 181 (the displacement is indicated by the arrow 182). Immediately following this, the piston rod is reversed to a position corresponding to the intended dose 181 (the displacement is indicated by the arrow 183). The intended dose is indicated by the double arrowed line 181, and the dose corresponding to the 'overshoot' by the double arrowed line 184.

According to the invention, the dripping from the needle is reduced by reversing the piston rod to release the pressure. To achieve the intended dose 181, a corresponding corrective movement 182 in the forward direction must be compensated for by reversing the piston 122 as shown by arrow 183. (IU=International Unit, 100 IU=1 ml), for example, is achieved by moving the piston 11 IU ahead followed by a retraction of one IU (referred to the outer face of the piston). The degree of compensation may depend on the size of the dose and the time it takes to inject, physical dimensions and materials of the cartridge, piston, outlet with needle, the viscosity of the liquid medication, the applied pressure, etc. In a preferred embodiment, the microcomputer 17 is used to determine the most suitable compensation pattern based on the parameters mentioned in order to make the compensation as accurate and effective as possible. A software program containing a model based on the mentioned parameters and fed with information on the actual physical set-up and the intended dose (the latter optionally input by the user via the I/O-device 15) is executed to control the electromotor 19 and thus the movement of the piston 122 via the piston rod 18 and the driving means 13.

Some preferred embodiments have been shown in the foregoing, but it should be stressed that the invention is not limited to these, but may be embodied in other ways within the subject-matter defined in the following claims. The invention may e.g. be used in pen type (longitudinal devices limited by the dimensions of the cartridge and the piston rod) or doser type (more compact devices, possibly using a bended piston rod) injection devices or in pump type infusion devices for continuous delivery.

What is claimed is:

1. A method for delivering an intended dose of medication from a medical injection device containing a cartridge that contains medication and that has moveable piston having an inner wall with an inner wall face that is in contact with the medication, an opposite outer wall having an outer wall face, the inner and outer wall faces being spaced apart from each other, wherein the spacing between the inner and outer wall decreases temporarily after the exertion of a force on the outer wall the method comprising the steps of:
   a. selecting a dose of medication to deliver;
   b. advancing the outer wall a distance D, the distance D being equal to the sum of:
      (i) a first distance D1 that is equal to an amount of displacement necessary that the inner face must move to deliver the dose selected in step a, and
      (ii) an overshoot distance OD; and
   c. retracting the outer wall by the overshoot distance OD.

2. The method of claim 1, wherein steps b(i) and b(ii) are performed sequentially and without a pause between steps b(i) and b(ii) thereby resulting in a smooth and continuous displacement.

3. The method of claim 1, wherein the overshoot distance OD step b(ii) and of retraction in step c are derived from an empirical rule.

4. The method of claim 3, wherein the empirical rule relies on one or more of the following parameters:
   a. type of medication,
   b. cartridge dimensions,
   c. cartridge material,
   d. outlet size of cartridge,
   e. viscosity of the medication within the cartridge, and
   f. applied pressure.

5. A medication device comprising: a cartridge containing a medication, the cartridge comprising:
   a. a moveable piston having a moveable inner wall having an inner wall face contacting the medication in the cartridge and a moveable outer wall having an outer wall face that faces in a direction opposite the inner wall face, the piston being flexible such that the outer wall moves closer to the inner wall when a force is exerted on the outer wall during medication delivery, a piston rod that drives the piston in the cartridge;
   b. a piston rod for driving the outer wall of the piston toward the medication in the cylinder;
   c. a drive means for driving the piston rod;
   d. a control means for controlling the drive means to drive the piston rod to a first distance D1 corresponding to an amount that the piston's inner wall must move to delivery a selected dose of medication; and
   e. wherein the control means is configured to advance further the piston rod an overshoot distance OD beyond the first distance D1 that the inner wall must move to deliver the dose and then, after the inner wall has been moved a distance D1, to refract the piston rod by amount equal to the overshoot distance OD.

6. The medication device of claim 5, wherein the overshoot distance OD is determined by an empirical rule that considers one or more of the following parameters:
   i. type of medication,
   ii. cartridge dimensions,
   iii. cartridge material,
   iv. outlet size of cartridge,
   v. viscosity of the medication within the cartridge, and
   vi. applied pressure.

7. A medication delivery device for delivering medication from a cartridge containing a moveable piston having a moveable inner wall with an inner wall face contacting medication in the cartridge, an outer wall having an outer wall face for engaging a piston rod, the inner and outer walls initially spaced apart from each other by a predetermined spacing, the spacing temporarily decreasing as force is exerted on the outer wall to advance the piston but returning to the predetermined spacing after the piston is moved by the force, the delivery device comprising:
   a. a linearly displaceable piston rod for engaging the outer wall of the piston in the cartridge to expel medication from the cartridge;
   b. a motor means for driving the piston rod; and
   c. an electronic processor for controlling the motor means, the processor configured to:
      i. receive a selected dose from a user,
      ii. advance the piston rod a first distance greater than the amount that the inner wall must move in order to to deliver the desired dose;
      iii. retract the piston rod by a second distance and at a rate that keeps the inner wall face from moving during step c(iii).

* * * * *